United States Patent
Hadley et al.

(10) Patent No.: US 10,820,859 B2
(45) Date of Patent: Nov. 3, 2020

(54) SYSTEMS AND METHODS FOR DETECTING PULSE WAVE VELOCITY

(71) Applicant: Stryker Corporation, Kalamazoo, MI (US)

(72) Inventors: Sean Hadley, St. Joseph, MI (US); Marko N. Kostic, Portage, MI (US); Joshua Elmer Mix, Portage, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1266 days.

(21) Appl. No.: 14/884,222

(22) Filed: Oct. 15, 2015

(65) Prior Publication Data

US 2016/0120411 A1    May 5, 2016

Related U.S. Application Data (60) Provisional application No. 62/072,669, filed on Oct. 30, 2014.

(51) Int. Cl.
*A61B 5/00* (2006.01)
*A61B 5/0205* (2006.01)
(Continued)

(52) U.S. Cl.
CPC ........ *A61B 5/6833* (2013.01); *A61B 5/02055* (2013.01); *A61B 5/02125* (2013.01);
(Continued)

(58) Field of Classification Search
CPC ... A61B 5/026; A61B 5/0261; A61B 5/02125; A61B 5/02416; A61B 5/681;
(Continued)

(56) References Cited

U.S. PATENT DOCUMENTS

| | | | | |
|---|---|---|---|---|
| 5,154,680 A | * | 10/1992 | Drzewiecki | ............ A61B 5/021 600/485 |
| 6,280,390 B1 | | 8/2001 | Akselrod et al. | |

(Continued)

FOREIGN PATENT DOCUMENTS

| | | |
|---|---|---|
| EP | 0443267 A1 | 12/1990 |
| WO | 2013001265 A2 | 1/2013 |
| WO | 2014165049 A1 | 10/2014 |

OTHER PUBLICATIONS

"How pulse oximeters work explained simply," dounloaded from http://www.howequipmentworks.com on Aug. 20, 2014.

*Primary Examiner* — Jeffrey G Hoekstra
*Assistant Examiner* — Jason M Ip
(74) *Attorney, Agent, or Firm* — Warner Norcross + Judd LLP (57) ABSTRACT

A non-invasive sensor unit adapted to be coupled to a patient includes a pair of light emitters spaced apart a known distance, and a pair light detectors. The light detectors detect light emitted from the emitters and scattered by a patient. The unit determines one or more cardiovascular characteristics of the patient from the scattered light, such as the patient's pulse wave velocity; a saturation of peripheral oxygen (SpO$_2$) level; a temperature; a respiration rate; a heart rate; and a blood pressure. The light emitters emit light that may have wavelengths between 600 and 1000 nanometers. The unit, in some embodiments, is integrated into a patch adapted to be secured to the skin of the patient. Readings from the unit may be transmitted to a separate device spaced from the unit, such as via Bluetooth, WiFi, or by other means.

16 Claims, 6 Drawing Sheets

(51) Int. Cl.
  *A61B 5/021* (2006.01)
  *A61B 5/1455* (2006.01)
  *A61B 5/024* (2006.01)
  *A61B 5/08* (2006.01)

(52) U.S. Cl.
  CPC ......... *A61B 5/02416* (2013.01); *A61B 5/0816* (2013.01); *A61B 5/14551* (2013.01)

(58) Field of Classification Search
  CPC .............. A61B 5/02438; A61B 5/6824; A61B 5/02108; A61B 5/0077; A61B 5/0285
  See application file for complete search history.

(56) References Cited

U.S. PATENT DOCUMENTS

| | | |
|---|---|---|
| 6,331,162 B1 | 12/2001 | Mitchell |
| 6,397,099 B1 * | 5/2002 | Chance ................ A61B 5/0059 600/323 |
| 7,544,168 B2 | 6/2009 | Nitzan |
| 7,674,231 B2 | 3/2010 | McCombie et al. |
| 7,803,120 B2 | 9/2010 | Banet et al. |
| 8,180,437 B2 | 5/2012 | Ohki et al. |
| 2009/0275841 A1 * | 11/2009 | Melendez ................ A61B 5/00 600/476 |
| 2011/0118564 A1 | 5/2011 | Sankai |

\* cited by examiner

SYSTEMS AND METHODS FOR DETECTING PULSE WAVE VELOCITY

CROSS-REFERENCE TO RELATED APPLICATIONS

This application claims priority to U.S. provisional patent application Ser. No. 62/072,669 filed Oct. 30, 2014, by inventors Sean Hadley et al. and entitled SYSTEMS AND METHODS FOR DETECTING PULSE WAVE VELOCITY, the complete disclosure of which is hereby incorporated herein by reference.

BACKGROUND

The present disclosure relates to devices, systems, and methods for determining a pulse wave velocity of a person.

The pulse wave velocity of a person is measurement of how fast a pressure wave travels through one or more blood vessels of the person. Knowledge of a person's pulse wave velocity can be used to estimate a person's blood pressure and/or to provide an indication of the cardiovascular health of the person. Changes in the pulse wave velocity are also indicative of the cardiovascular state of the person.

SUMMARY

According to various embodiments, the present disclosure provides devices, systems, and methods for non-invasively determining a person's pulse wave velocity. In some embodiments, a device, system, and/or method is provided that compares pulse wave velocities determined at different locations on the person's body. In still other embodiments, a device, system, and/or method is provided that monitors changes in the person's arterial stiffness over time and/or analyzes such changes to provide a more complete clinical profile of the person's cardiovascular health. In still other embodiments, the system, device, and/or method allows caregivers to easily attach one or more sensors to the person that directly measure pulse wave velocity without the need for also attaching any ECG electrodes, or other types of sensors.

According to one embodiment, a sensor unit is provided that is adapted to be non-invasively coupled to a patient. The sensor unit includes first and second light emitters, as well as a plurality of first light detectors and a plurality of second light detectors. The first light detectors are adapted to detect a portion of first light that is emitted by the first light emitter and scattered by the patient. The second light detectors are adapted to detect a portion of second light emitted by the second light emitter and scattered by the patient. The sensor unit further includes a controller in communication with the first light detectors and with the second light detectors. The controller determines a pulse wave velocity of the patient using the known distance between the first and second light emitters and an output from at least one of the first light detectors and an output from at least one of the second light detectors.

In another embodiment, the first light detectors are positioned at different distances from the first light emitter, and the second light detectors are positioned at different distances from the second light emitter. The controller, in at least one embodiment, selects at least one of the plurality of first light detectors and at least one of the plurality of second light detectors based upon how deep into the patient the pulse wave velocity determination is to be based.

In another embodiment, the plurality of first light detectors includes a first subset of first light detectors positioned a first distance from the first light emitter and a second subset of first light detectors positioned a second distance from the first light emitter. Still further, the plurality of second light detectors includes a third subset of second light detectors positioned the first distance from the second light emitter and a fourth subset of second light detectors positioned the second distance from the second light emitter. The sensor unit, in an embodiment, selects one of the first and second subsets based upon how deep into the patient the pulse wave velocity determination is to be based, and the controller uses the selected subset in determining the pulse wave velocity. In another embodiment, the controller is also adapted to select at least one of the first light detectors from the selected first or second subset based upon an orientation of the sensor unit relative to the patient's adjacent arterial structure. The controller uses the selected at least one of the first light detectors when determining the pulse wave velocity.

In still another embodiment, the sensor unit includes a transmitter that wirelessly transmits the pulse wave velocity to at least one of the following: a cell phone, a computer, a patient support apparatus, and a local area network.

The controller repetitively determines the pulse wave velocity of the patient. The controller also detects changes in the pulse wave velocity of the patient over time, in at least one embodiment.

The first light and second light have wavelengths between 600 and 1000 nanometers in some embodiments.

The sensor unit may further be adapted to measure at least one of the following patient conditions: a saturation of peripheral oxygen ($SpO_2$) level; a temperature; a respiration rate; a heart rate; and a blood pressure. In some embodiments, the sensor is further configured to allow a user to select an approximate penetration depth of the first or second light that is scattered by the patient and sensed by the sensor.

In still another embodiment, the first and second light detectors are integrated into a patient support, such as, but not limited to, a top surface of a mattress or cushion for a bed, a stretcher, a cot, an operating table, and/or a recliner.

In still another embodiment, the first and second light emitters, the controller, and the pluralities of first and second light detectors are all integrated into a patch adapted to be adhesively secured to the skin of the patient.

According to another embodiment, a sensor unit is provided that is adapted to be non-invasively coupled to a patient. The sensor unit includes a first light emitter, a second light emitter spaced from the first light emitter a known distance, a first light detector adapted to detect a portion of first light that is emitted by the first light emitter and scattered by the patient, and a second light detector adapted to detect a portion of second light emitted by the second light emitter and scattered by the patient. The sensor unit further includes a housing, a controller contained with the housing, and a patch physically coupled to the housing. The controller is in communication with the first and second light detectors and is adapted to determine a pulse wave velocity of the patient using outputs from the first and second light detectors and the known distance. The patch is adapted to secure the first light emitter, the first light detector, the second light emitter, and the second light detector to the skin of the patient.

In another embodiment, a transmitter is included within the housing and is adapted to transmit the pulse wave velocity to a remote location. The transmitter transmits, in at least one embodiment, the pulse wave velocity to at least one of the following: a cell phone, a computer, a local area network, and a patient support apparatus.

In still another embodiment, the controller turns off the first light emitter, determines first outputs from each of the plurality of first light detectors while the first light emitter is turned off, and uses the first outputs to determine an intensity of the first light that is scattered by the patient while the first light emitter is turned on. The controller may further turn off the second light emitter, determine second outputs from each of the plurality of second light detectors while the second light emitter is turned off, and use the second outputs to determine an intensity of the second light that is scattered by the patient while the second light emitter is turned on.

According to still another embodiment, a method of evaluating a patient is provided that includes providing a sensor unit having a first light emitter, a first light detector, a second light emitter, and a second light detector. The first light emitter is spaced from the second light emitter a known distance. The method further includes attaching the sensor unit to the patient at a first location; determining a first pulse wave velocity of the patient at the first location using the sensor unit; attaching the sensor unit to the patient at a second location; determining a second pulse wave velocity of the patient at the second location using the sensor unit; and comparing the first and second pulse wave velocities.

In other embodiments, the method includes issuing an alert if the first and second pulse wave velocities differ by more than a threshold. The alert is indicative of the potential of a localized vascular condition at either the first or second location of the patient.

The method also includes, in at least one embodiment, detecting a pulse wave at the first location by emitting first light from the first light emitter and detecting a portion of the first light that is scattered by the patient using the first light detector; as well as detecting the pulse wave at the first location by emitting second light from the second light emitter and detecting a portion of the second light that is scattered by the patient using the second light detector.

The method may also include measuring at least one of the following patient conditions with the sensor unit: a saturation of peripheral oxygen ($SpO_2$) level; a temperature; a respiration rate; a heart rate; and a blood pressure.

The step of attaching the sensor unit to the patient at first and second locations includes securing the adhesive patch to the skin of the patient, in at least one embodiment.

According to another embodiment, a method is provided for evaluating a patient that includes: (a) providing a sensor unit having a first light emitter, a first light detector, a second light emitter, and a second light detector, the first light emitter being spaced apart from the second light emitter a known distance; (b) attaching the sensor unit to the patient; (c) emitting first light from the first light emitter and detecting a portion of the first light that is scattered by the patient using the first light detector; (d) emitting second light from the second light emitter and detecting a portion of the second light that is scattered by the patient using the second light detector; (e) estimating a first arterial stiffness using outputs from the first and second light detectors during steps (c) and (d); (f) repeating at least steps (c) through (d) and estimating a second arterial stiffness using outputs from the first and second light detectors during the repeated steps (c) and (d); and (g) comparing the first and second estimates of arterial stiffness.

In other embodiments, the method includes displaying information indicating an increase or decrease in the arterial stiffness over time wherein the information is based at least partially on the first and second estimates of arterial stiffness.

The method also includes, in at least one embodiment, determining a first pulse wave velocity using the outputs of the first and second light detectors during steps (c) and (d); and determining a second pulse wave velocity using the outputs of the first and second light detectors during the repeated steps (c) and (d). The first light emitter, first light detector, second light emitter, and second light detector are all integrated into a common housing in some embodiments.

According to another embodiment, a sensor unit is provided that is adapted to be non-invasively coupled to a patient. The sensor unit includes a first light emitter, a first light detector, a second light emitter spaced from the first light emitter a known distance, a second light detector, a housing, a transmitter, and a patch. The first light detector detects a portion of first light that is emitted by the first light emitter and scattered by the patient. The second light detector detects a portion of second light emitted by the second light emitter and scattered by the patient. The transmitter is contained within the housing and transmits data generated from the first and second light detectors to a remote device. The patch is physically coupled to the housing and is adapted to secure the first light emitter, the first light detector, the second light emitter, and the second light detector to the skin of the patient.

The patch may include a plurality of first light detectors equally spaced from the first emitter and a plurality of second light detectors equally spaced from the second emitter. The data transmitted by the transmitter includes data from both the plurality of first light detectors and the plurality of second light detectors.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
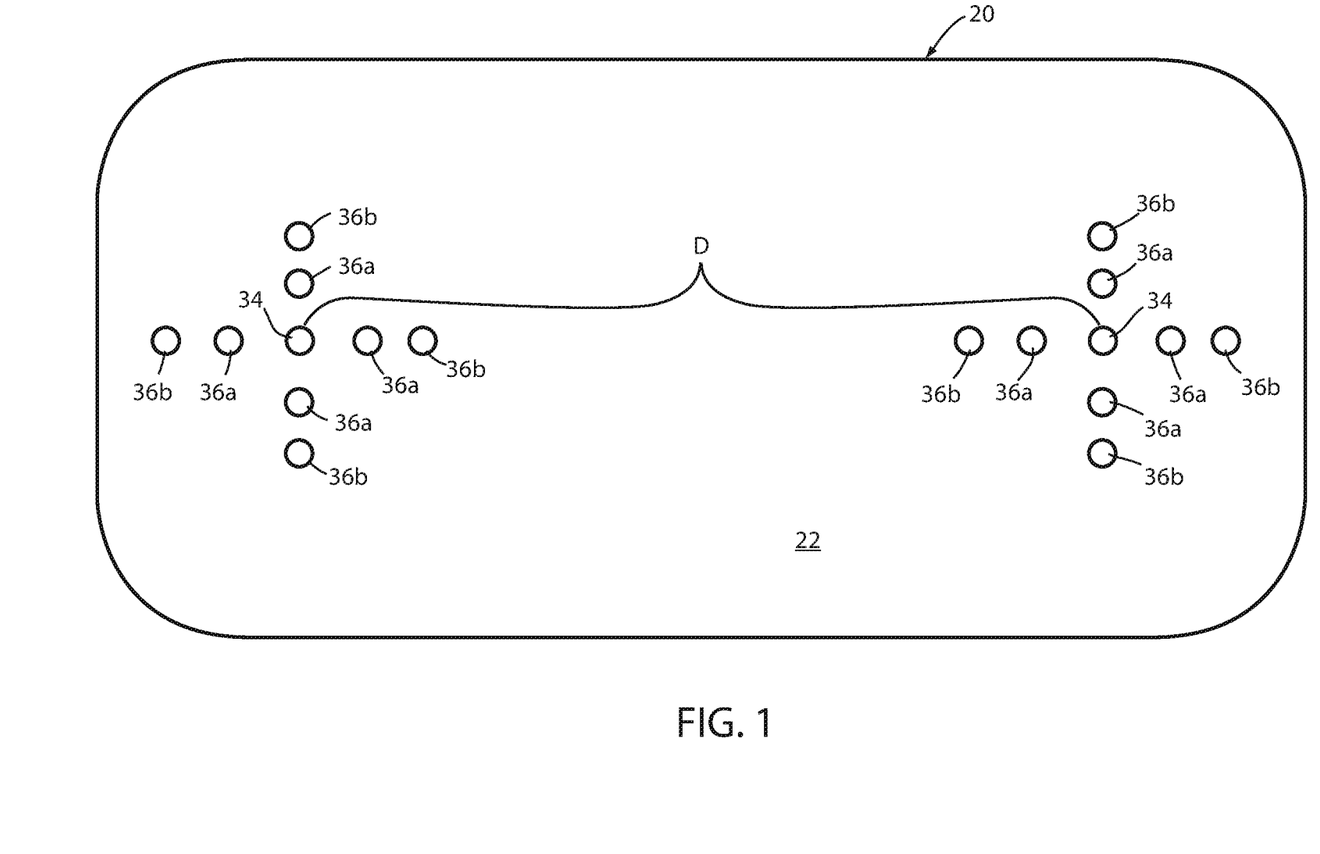
FIG. 1 is a bottom view of a sensor unit according to one embodiment of the present disclosure.

An underside 22 of a sensor unit 20 according to one embodiment is shown in FIG. 1. Sensor unit 20 is adapted to take readings from a person that can be used to determine the person's pulse wave velocity. In the embodiment shown in FIG. 1, sensor unit 20 determines the person's pulse wave velocity. In other embodiments, such as will be described in greater detail below, sensor unit 20 is configured to take readings and transmit the raw data from the readings to a remote device that processes the readings to determine the person's pulse wave velocity. In still other embodiments, sensor unit 20 is configured to determine one or more additional physiological characteristics of the person, such as, but not limited to, temperature, respiration rate, heart rate, saturation of peripheral oxygen ($SpO_2$), heart rate variability, arterial stiffness, and/or blood pressure.

Figure 2:
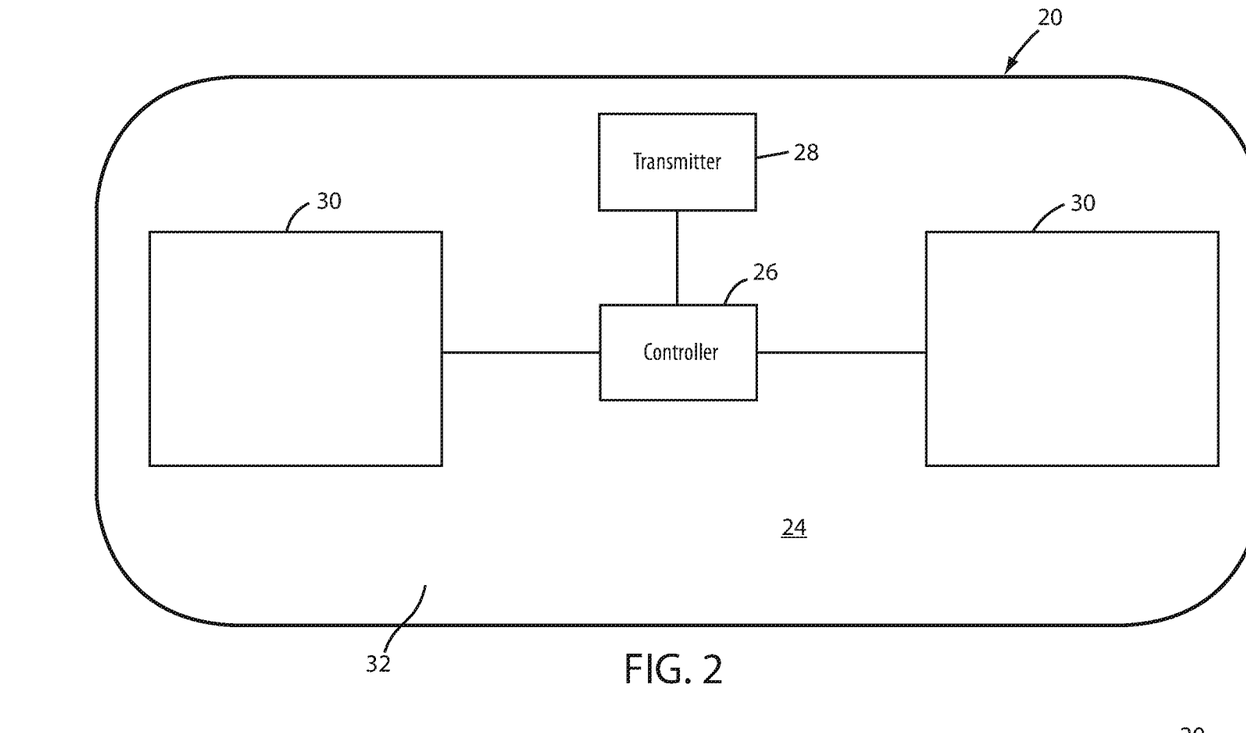
FIG. 2 is a top view of the sensor unit of FIG. 1.

As shown in FIG. 2, sensor unit 20 includes a top side 24 having a controller 26, a transmitter 28, and two pulse wave sensors 30. Controller 26, transmitter 28, and pulse wave sensors 30 are secured to a flexible layer of material that forms a patch 32. In one embodiment, underside 22 of patch 32 includes adhesive in one or more areas that allows unit 20 to be selectively adhered to the skin of the person whose pulse wave velocity is to be determined. In other embodiments, patch 32 is secured to the person without the use of adhesive, such as through one or more straps, ties, or other structures that enable sensor unit 20 to be suitably stabilized on the person's skin while pulse wave velocity readings are taken.

As shown in FIG. 1, each pulse wave sensor 30 includes an emitter 34 and a plurality of detectors 36 positioned within the vicinity of the associated emitter 34. Each emitter is adapted to emit light onto the patient's skin. Some of that light will be absorbed by the patient's skin and internal tissue, while some of that light will be scattered back toward sensor unit 20. The scattered light is detected by one or more of detectors 36, as discussed in greater detail below.

In one embodiment, emitters 34 emit infrared light. More specifically, in one embodiment, emitters 34 emit infrared light having a wavelength of approximately 940 nanometers. In another embodiment, emitters 34 emit light having a wavelength of approximately 660 nanometers. In still another embodiment, emitters 34 emit light having any wavelength between about 600 and 1000 nanometers. In still other embodiments, multiple emitters 34 are used that emit light having different wavelengths, or a single emitter 34 is used that is adapted to emit light having different wavelengths, such as, but not limited to, wavelengths of approximately 940 nanometer and 660 nanometers.

Each pulse wave sensor 30 is generally configured to generate a photoplethysmogram reading that corresponds to the changing volume of oxygenated blood in the patient's tissue underneath each emitter 34. That is, the light emitted by each emitter 34 will be absorbed and scattered in differing amounts depending upon the amount of oxygenated blood present in the adjacent tissue. As the pressure wave in the blood creating by the pumping of the person's heart passes through the one or more arteries and/or arterioles adjacent the emitter, the volume of oxygenated blood in these blood vessels will rise. That is, the volume of oxygenated blood in the arterial structure adjacent the emitter 34 will increase with the relatively higher pressure of the pulse wave and decrease with the relatively lower pressure between the pulse waves. This differing volume is detected by the different amounts of light that is scattered back to detectors 36 (after being emitted by emitters 34). The scattered light detected at detectors 36 is repetitively measured and yields a waveform 38, such as waveform 38 shown in FIG. 5, which is an illustrative waveform 38 generated by one of pulse wave sensors 30.

Figure 3:
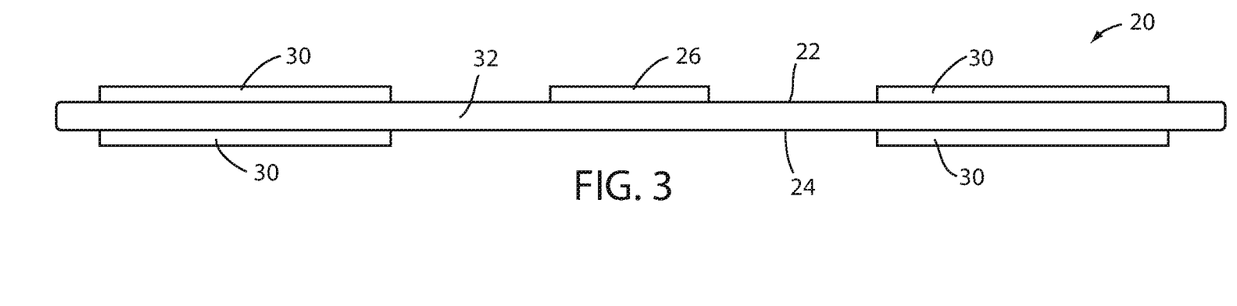
FIG. 3 is a side, elevation view of the sensor unit of FIG. 1

In the embodiment shown in FIGS. 1-3, sensor unit 20 includes two pulse wave sensors 30. Pulse wave sensors 30 are spaced apart a known distance D, such as illustrated in FIG. 1. Distance D may vary considerably in different embodiments. In at least one embodiment, distance D is on the order of a few inches, although, as noted, distance D can be considerably smaller or larger than this. Distance D is measured or calculated prior to usage of sensor unit 20 and its value is stored in a memory accessible to controller 26. As will be discussed in greater detail below, controller 26 uses distance D for determining the person's pulse wave velocity.

Controller 26 is constructed of any electrical component, or group of electrical components, that are capable of carrying out the functions described herein. In many embodiments, controller 26 is a conventional microcontroller, although not all such embodiments need include a microcontroller. In general, controller 26 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 26 in carrying out the functions described herein, as well as the data necessary for carrying out these functions are stored in a memory accessible to controller 26.

In at least one embodiment, controller 26, transmitter 28 and/or any of the electronic components of pulse wave sensors 30 are implemented as flexible electronics, thereby allowing the components, or portions of components, to more easily bend and/or follow the flexibility of patch 32, thereby enabling sensor unit 20 to more easily conform to the body of the person whose pulse wave velocity is being measured. Such flexible electronics may include flexible plastic substrates, such as polyimide, PEEK (Polyether ether ketone), conductive polyester film, and/or other flexible electronic technologies.

Controller 26 is configured to determine a person's pulse wave velocity by measuring how long it takes for one or more pulse waves detected at a first one of pulse wave sensors 30 to travel to the other one of pulse wave sensors 30. Known distance D is then divided by this time period, which results in a measurement of the person's pulse wave velocity. Controller 26 is configured in at least one embodiment to repetitively take measurements of the pulse wave velocity. The repetitive measurements may be processed, filtered, and/or combined in other ways prior to making the readings available to a user. Such processing may include averaging multiple readings of the pulse wave velocity together and displaying—or otherwise making available to the user—this average reading.

Controller 26 measures how long it takes for one or more pulse waves to travel between the two pulse wave sensors 30 of sensor unit 20 by comparing the waveforms 38 generated from each pulse wave sensor, correlating the waveforms 38—or one or more landmarks of the waveforms 38 (e.g. crests, troughs, etc.)—to each other, and measuring the time offset between them. This process can be more easily understood with reference to FIG. 4.

Figure 4:
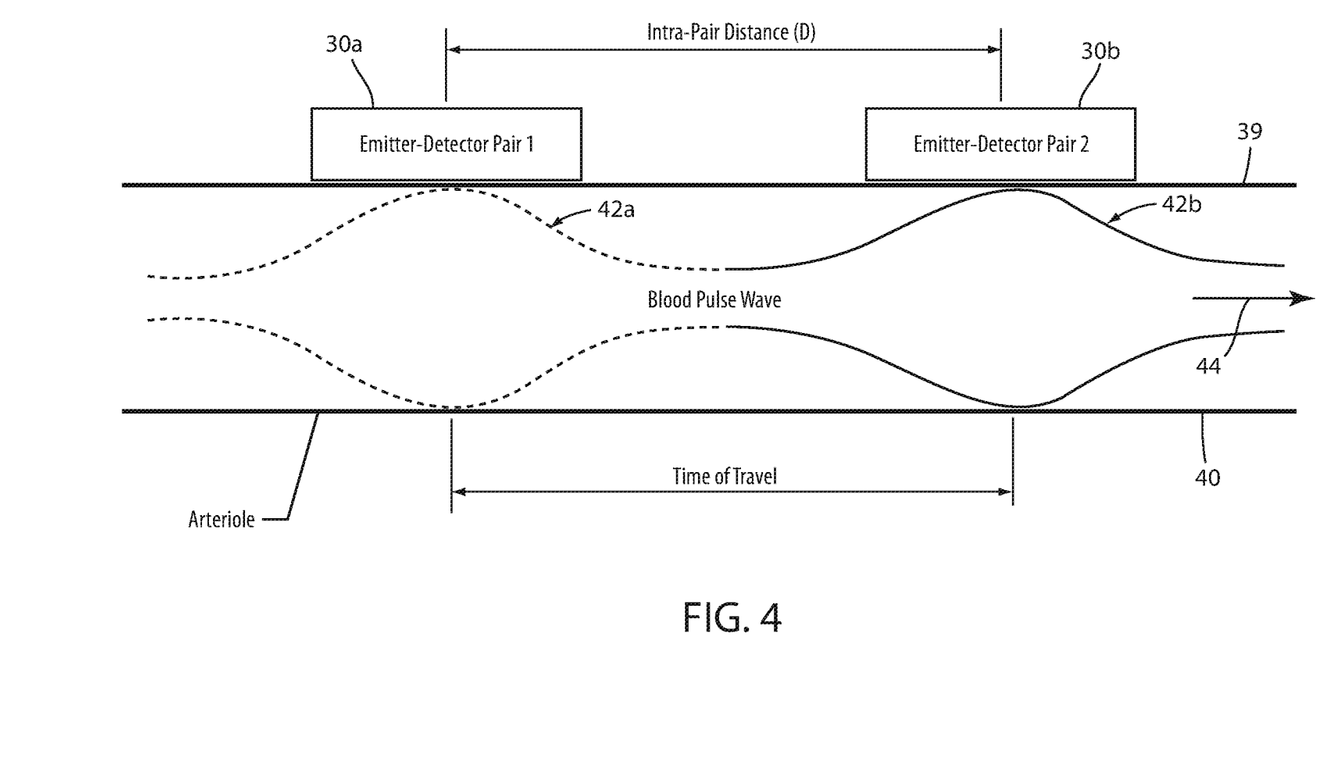
FIG. 4 is a diagram illustrating movement of a blood pulse wave and emitter-detector pairs of the sensor unit of FIG. 1.

FIG. 4 illustrates a first pulse wave sensor 30a and a second pulse wave sensor 30b that are spaced apart from each other distance D. Each pulse wave sensor 30 is placed in contact with a person's skin 39. An arteriole 40 of the person is illustrated diagrammatically at a location underneath the person's skin. Two successive blood pulse waves 42a and 42b are shown in FIG. 4. Blood pulse waves 42a and 42b are traveling in a direction indicated by arrow 44. At the moment in time, $T_1$, shown in FIG. 4, first pulse wave 42 is passing by first pulse wave sensor 30a. That is, an amplitude of the waveform 38 detected by pulse wave sensor 30a is at its crest. At a subsequent moment in time, $T_2$, not shown in FIG. 4, first pulse wave 42a will pass by second pulse wave detector 30b. Controller 26, which is in communication with both sensors 30a and 30b, records both times $T_1$ and $T_2$, and determines the difference between these two times. Controller 26 then divides the distance D by this time difference to compute a pulse wave velocity.

In one embodiment, not shown in FIGS. 1-3, sensor unit 20 includes a display for displaying the calculated pulse wave velocity. In another embodiment, also not shown, sensor unit 20 includes a user interface that allows a user to display other items, such as past measurements of pulse wave velocities which are stored in a memory within sensor unit 20. Indeed, in some embodiments, the display on sensor unit 20 is capable of displaying a graph of the person's pulse wave velocity over a selected time period, as well as comparisons of the person's current pulse wave velocity with prior readings. Data may also be stored on the sensor unit of readings from other patients, as well as other data discussed below. In still other embodiments, any or all of the data generated by sensor unit 20 is transmitted to a remote device, such as a computer, smart cell phone, local area network, or other electronic processing unit that is capable of analyzing, displaying, and/or storing the data.

As is shown in FIG. 1, each pulse wave sensor 30 of sensor unit 20 includes a set of detectors 36. More specifically, each pulse wave sensor 30 includes a first subset of detectors 36a that are positioned a first distance away from the emitter 34, and a second subset of detectors 36b that are positioned a second distance away from the emitter 34. Additional subsets may be included that are positioned at other distances away from emitter 34 where all detectors 36 within a given subset are positioned the same distance away from emitter 34. When determining a person's pulse wave velocity, controller 26 is configured in at least one embodiment to analyze readings from the same subset of detectors 36 in both of the pulse wave sensors 30. That is, if controller 26 generates a first waveform 38 using readings from detectors 36b from first pulse wave sensor 30, controller 26 will likewise generate a second waveform 38 using readings from detectors 36b from second pulse wave sensor 30 (and not detectors 36a). This is done because the detectors 36 from the different subsets will measure light scattering that occurs at different depths within the patient's tissue, as can be seen more clearly with respect to FIG. 6.

Figure 6:
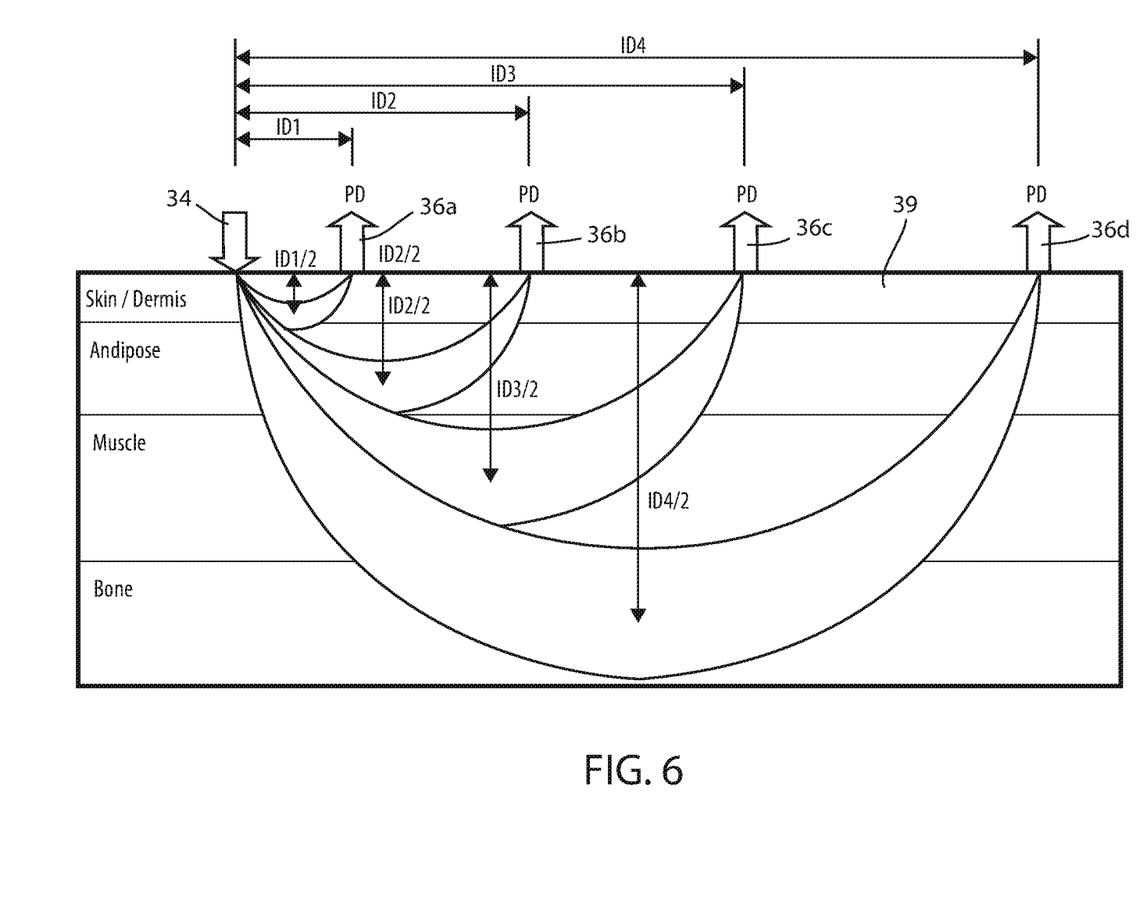
FIG. 6 is a diagram illustrating an emitter/detector configuration that may be used with any of the sensor units disclosed herein to take measurements at different depths.

FIG. 6 illustrates an emitter 34 positioned on the skin 39 of a person, as well as four detectors 36a, 36b, 36c, and 36d. Each detector 36a, 36b, 36c, and 36d is positioned away from emitter 34 a distance ID1, ID2, ID3, and ID4, respectively. The scattered light that is detected by detector 36a is light that has generally penetrated into the patient's tissue a distance that is approximately equal to one-half of the distance ID1. That is, detector 36a will detect scattered light that has penetrated a distance approximately equal to half of its distance from emitter 34. Similarly, detector 36b will detect light that has penetrated into the person's tissue a distance approximately equal to ½ ID2. Detectors 36c and 36d will detect light that has penetrated into the person's tissue a distance approximately equal to ½ ID3 and ½ ID4, respectively.

In the embodiment shown in FIG. 1, sensor unit 20 only includes two subsets of detectors 36a and 36b, rather than the four subsets of detectors shown in FIG. 6 (36a, b, c, and d). In one embodiment, controller 26 is configured to allow a user to select which depth the pulse wave velocity measurements are to be taken. That is, controller 26 is adapted to allow a user to select whether to use readings from one or more detector(s) 36a in the first subset or one or more detectors 36b in the second subset. Alternatively, or in addition, controller 26 is configured in at least one embodiment to automatically make the selection of which subset of detectors 36a, 36b . . . to utilize in determining the person's pulse wave velocity. When making this selection automatically, controller 26 is configured in one embodiment to select the subset that includes detectors 36 having the greatest signal strength. In other embodiments, different factors may be used by controller 26 for automatically selecting which subset of detectors to use.

In at least one embodiment, after the subset of detectors 36 has been chosen—whether automatically or manually—controller 26 is configured to combine all of the readings from the detectors 36 in that chosen subset when calculating the pulse wave velocity. In one embodiment, the combination is a simple average of the readings from all of the detectors 36 within that subset. In another embodiment, the combination is based on other factors, such as, but not limited to, a weighted average, a correlation with one or more detector readings from the other pulse wave sensor 30, or still other factors.

In still another embodiment, once a subset of detectors 36 has been chosen—whether automatically or manually—controller 26 is configured to select only a single one of the detectors 36 within the given subset and use the outputs from that single detector 36 for calculating the person's pulse wave velocity. In one embodiment, controller 26 selects the detector 36 within the chosen subset that has the highest signal strength. In another embodiment, controller 26 correlates each of the waveforms 38 from each of the detectors 36 in the other pulse wave sensor 30 and selects the detector 36 whose waveform 38 has the highest correlation with the waveform from the other pulse wave sensor. In still other embodiments, controller 26 uses other criteria to select which one or ones of the detectors 36 within the chosen subset to use when determining a person's pulse wave velocity.

Controller 26 is also configured in at least one embodiment to allow a user to select different subsets of detectors 36 for use with each of the two pulse wave sensors 30. That is, in at least one embodiment, a user can select the detectors 36a of the first subset for use with a first one of the two pulse wave sensors and the user can also select the detectors 36b of the second subset for use with the second one of the two pulse wave sensors. This selection features allows the user to choose a depth range of the scattered light that is most appropriate for the anatomical location on the person's body adjacent each individual pulse wave sensor 30. Thus, for example, if one of the sensors 30 is positioned at an anatomical location that includes an easily detectable pulse wave near the surface of the person's skin (e.g. the inner wrist) and the other of the sensors 30 is positioned at another location where the corresponding arterial structure is more deeply positioned within the patient's body (e.g. at a location displaced from the wrist and closer to the person's elbow), the depth at which the measurements are taken by each of the sensors 30 can be varied to accommodate this. Thus, the sensor 30 positioned adjacent the person's arterial structure that is close to the person's skin may utilize readings from detectors 36a in the first subset of detectors, while the sensor 30 positioned adjacent the person's arterial structure that is deeper within the person's tissue may utilize readings from detectors 36c or 36d in the third or fourth subset of detectors.

Transmitter 28 of sensor unit 20 is, in at least one embodiment, a wireless transmitter adapted to transmit data to a separate device, such as, but not limited to, a smart phone, a wristband monitor, a tablet, a personal computer, a server, a network, or some other computing device. Transmitter 28 may be a Wi-Fi transmitter (e.g. IEEE 802.11), a Bluetooth transmitter (e.g. IEEE 802.15.1) or a ZigBee transmitter (i.e. IEEE 802.15.4). In still other embodiments, transmitter 28 is a wired transmitter, such as a USB (universal serial bus) port, or other type of communication port adapted to be physically coupled to a cable or other device. In still other embodiments, transmitter 28 is adapted to be able to communicate both by wire and wirelessly.

Figure 7:
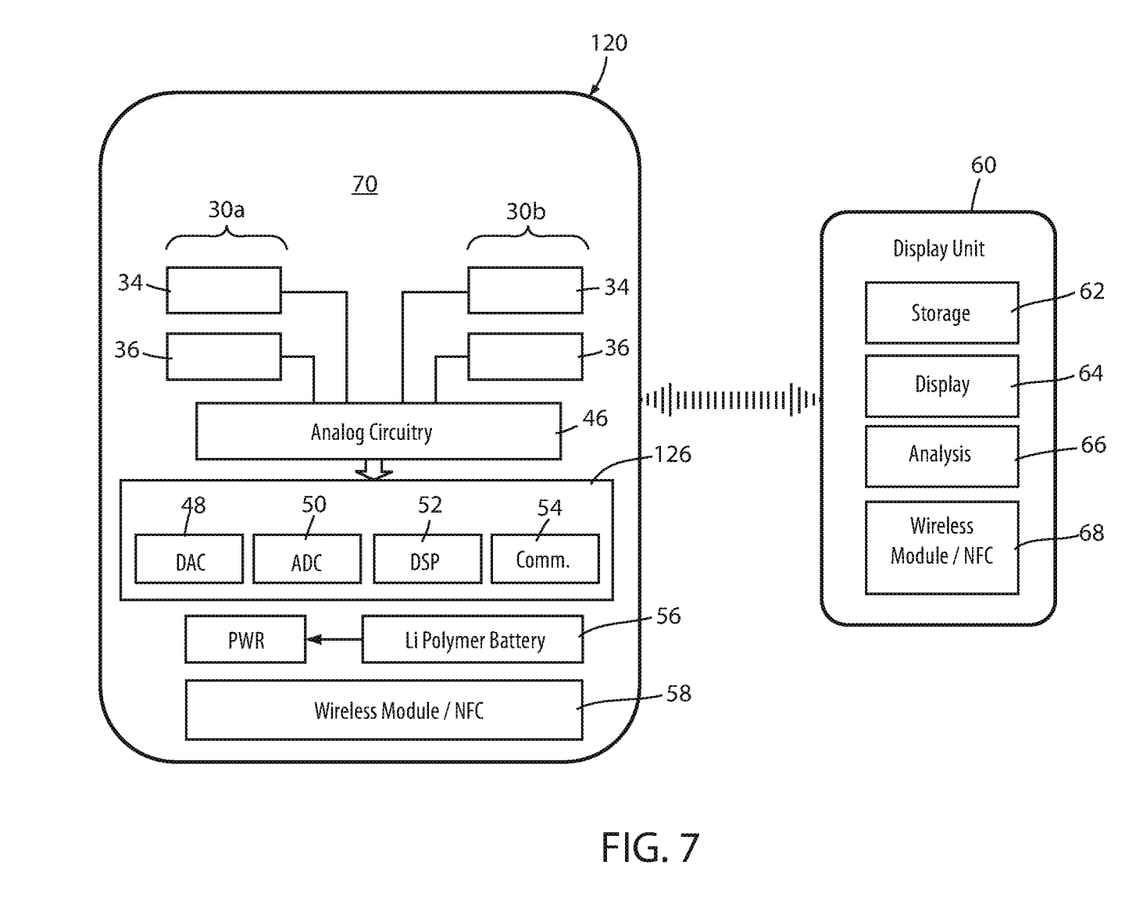
FIG. 7 is a diagram of another sensor unit according to the present disclosure in communication with a display unit.

FIG. 7. illustrates an alternative embodiment of a sensor unit 120 that operates generally in accordance with the principles discussed above with respect to sensor unit 20. That is, sensor unit 120 includes a pair of pulse wave sensors 30a and 30b that each utilizes at least one light emitter 34 and at least one light detector 36. The outputs from sensors 30a and 30b are fed to a set of analog circuitry 46 that suitably pre-processes the outputs before inputting them into a controller 126. Controller 126 includes one or more digital to analog converters (DAC) 48, one or more analog to digital converters (ADC) 50, one or more digital signal processors (DSP) 52, and one or more communication circuits (COMM) 54. In one embodiment, controller 126 is a microcontroller, although it will be understood by those skilled in the art that it may be implemented with other types of electronic circuitry, such as, but not limited to, any of the types of circuitry discussed above that may be used to implement controller 26.

Sensor unit 120 further includes a battery 56 that supplies power to controller 126, sensors 30, analog circuitry 46, and a wireless module 58. In the illustrated embodiment, battery 56 is a lithium polymer battery, although it will be understood that other types of batteries may be used. Still further, in some embodiments, sensor unit 120 includes a power cord for supplying power instead of, or in addition to, battery 56.

Wireless module 58 enables controller 126 to communicate with a separate device 60. Device 60 may be positioned in the same room as sensor unit 120, or it may be positioned at a more remote location. Device 60 is any one of a smart phone, a wristband monitor, a tablet computer, a personal computer, a server, a network, or some other computing device. Wireless module 58 may include a Wi-Fi transmitter (e.g. IEEE 802.11), a Bluetooth transmitter (e.g. IEEE 802.15.1) a ZigBee transmitter (i.e. IEEE 802.15.4), or a near field communication transmitter, such as, but not limited to, a transmitter that communicates in accordance with European Computer Manufacturers Association (ECMA) standard 340 and/or 352, or International Organization for Standardization and International Electrotechnical Commission (ISO/IEC) standard 18092 and/or 21481.

In at least one embodiment, device 60 is a person support apparatus equipped with near field communication abilities that enable the person support apparatus to communicate using near field communication with wireless module 58 of sensor unit 120. When implemented as a person support apparatus, device 60 may take on any of the forms, and include any of the features, of the person support apparatuses described in commonly assigned U.S. patent application Ser. No. 13/802,992 filed Mar. 14, 2013 by inventors Michael Joseph Hayes et al. and entitled COMMUNICATION SYSTEM FOR PATIENT SUPPORT APPARATUSES, the complete disclosure of which is hereby incorporated herein by reference. When wireless module 58 communicates with a person support apparatus, the data transmitted by sensor unit 120 is displayable on one or more displays on the person support apparatus. For example, if the person support apparatus is a hospital bed having an LCD screen, or other type of display, data received by the bed from sensor unit 120 is displayable on the bed's display. The bed, or other person support apparatus, may be further configured to transmit the data it receives from sensor unit 120 to an electronic medical records database, or to some other computer, server, or network service that the bed is in communication with via one or more other transceivers.

Device 60 includes a storage unit (e.g. electronic memory) for storing data received from sensor unit 120, as well as for storing instructions carried out by a processor 66 included within device 60. Device 60 also includes a display for displaying information, including, but not limited to, the data received from sensor unit 120. Such data may be displayed before any additional processing or analysis is carried out by processor 66, or it may be displayed after additional processing and/or analysis is carried out by processor 66, or both. Device 60 further includes a wireless module 68 that is compatible with the communication protocol used by wireless module 58 of sensor unit 120, thereby enabling wireless module 58 of sensor unit 120 to communicate with wireless module 68 of device 60. In at least one embodiment, such communication is bidirectional.

As was discussed previously, in at least one embodiment, sensor unit 120 is configured to process the outputs from pulse wave sensors 30 locally and determine the person's pulse wave velocity. These determinations of pulse wave velocity can then be communicated wirelessly to device 60 using wireless module 58. In an alternative embodiment, sensor unit 120 is configured to forward the outputs from the pulse wave sensors 30 to device 60 without performing the analysis necessary to determine the person's pulse wave velocity. In those instances, processor 66 of device 60 is programmed to analyze the data received from device 60 and determine the person's pulse wave velocity from this data. By performing the data analysis remotely (i.e. not on sensor unit 120 itself), controller 126 can be simplified and/or reduced in expense and/or size. Further, by performing the data analysis remotely (i.e. on device 60), large amounts of historical data from sensor unit 120 can be stored in storage unit 62 over lengthy periods of time.

In at least one embodiment, device 60 is adapted to communicate with multiple sensor units 120, either simultaneously or during non-overlapping time periods. When so configured, each sensor unit 120 includes a unique unit ID that distinguishes itself from other sensor units 120. Device 60 uses this unit ID to separate the data it receives from sensor units 120 and to communicate with individual ones of the multiple sensor units 120.

In some embodiments, device 60 has access to an electronic medical records (EMR) database, or at least the specific EMR corresponding to the person whose pulse wave velocity is being monitored. In those instances, device 60 is configured to forward the pulse wave velocity readings directly into the person's EMR without requiring an operator to manually transfer the data to the EMR.

In still other embodiments, device 60 is a smart phone having one or more apps that communicate with sensor unit 120 and allow a user to see, store, analyze, compare, and perform other manipulations of the data generated by sensor unit 120. In some embodiments, the app is further configured to generate an alert when the pulse wave velocity of the person exceeds a threshold, or otherwise changes in a way that meets one or more criteria, which may be user-configurable. In still other embodiments, the app is configured to send a message to one or more other devices when the pulse wave velocity reading meets one or more criteria. The messages include, in at least one embodiment, an email, a text message, and/or a phone call that is transmitted to a smart phone, computer, or other device associated with one or more healthcare professionals. In this manner, one or more healthcare professionals can be kept apprised of relevant changes in the pulse wave velocity—or other vascular characteristics measured by sensor unit 120—of the person wearing sensor unit 120.

Sensor unit 120 includes a substrate 70 to which the various other components of sensor unit 120 (e.g. sensors 30, analog circuitry 46, controller 126, etc.) are attached. In one embodiment, substrate 70 is a flexible material that can be wrapped, either wholly or partially, around a person's arm, leg, torso, or other body part at the location where the pulse wave velocity is to be measured. As with sensor unit 20 discussed above, substrate 70 may include one or more locations in which an adhesive is applied to thereby allow sensor unit 120 to be adhesively coupled to a desired location on the person's body.

Sensor units 20 and 120 can be coupled to any location on a person's body where pulse wave velocity readings are desirably taken. When positioning sensor unit 20 or 120 on the person's body, it is not necessary to precisely align sensor unit 20 or 120 with the longitudinal extent of the patient's arterial structure adjacent the sensor unit. Instead, sensor unit 20 and/or 120 need only be placed in general alignment with the arterial structure adjacent the sensor unit. Thus, for example, if sensor unit 20 or 120 is attached to a person's leg or arm, sensor unit 20 or 120 should be attached thereto such that a straight line connecting sensors 30 of the sensor unit are generally parallel to the longitudinal extent of the person's arm or leg. Precise alignment with arterial structure, however, is not required. This is also true if the sensor unit 20 or 120 is attached to a person's torso. In such cases, the imaginary line connecting sensors 30 should point generally toward the person's heart, but need not exactly intersect the location of the person's heart. In general, sensor units 20 and 120 may be placed in any orientation so long as the arterial structure monitored by one of the sensors 30 is either predominantly upstream or predominantly downstream of the arterial structure monitored by the other one of the sensors 30.

In at least one of the embodiments of each of sensor units 20 and 120, controllers 26 and 126 are modified to remove or substantially eliminate optical noise detected at detectors 36. In one embodiment, an optical filter is included with each detector 36 that filters out all light other than light having the same frequency as emitter 34. In another embodiment, sensor units 20 and/or 120 use an optical chopping method to filter out light that originates from a source other than emitter 34. The optical chopping method is described more below.

Sensor units 20 and/or 120, when configured with an optical chopping filter, take readings from detectors 36 when no light is being emitted from emitter 34. These light readings correspond to the scattering of any ambient light that originates from a source other than emitter 34. Controller 26 and 126 record these ambient readings and use them to filter out the portion of the light that is detected while emitter 34 is illuminated, but which originates from a source other than emitter 34. Controller 26 and 126 achieve this by subtracting the ambient light reading from the readings of detector 36 taken when emitter 34 is illuminated. The readings from detector 36 taken when emitter 34 is illuminated will include light that originates from emitter 34 as well as one or more ambient sources. By subtracting from this total detector reading, only that portion of the detected light which originated from emitter 34 is measured.

In at least one embodiment, an ambient light reading is taken before each reading taken when emitter 34 is illuminated. After each ambient light reading, controller 26 and 126 take a reading from detector(s) 36 while emitter 34 is illuminated and subtract the latest ambient light reading from that latest total reading. In other words, in this embodiment, every other reading taken is one in which emitter 34 is not illuminated. Those readings that are taken when emitter 34 is illuminated are processed by subtracting from them the ambient light reading made either immediately before or immediately after. In still other embodiments, ambient light readings are taken less frequently than every other reading. Regardless of the frequency of the ambient light readings, controller 26 and 126 take readings at a rate that is on the order of 1000 times per second in at least some embodiments.

Still further, in at least one embodiment of sensor units 20 and 120, controllers 26 and 126 are configured to issue an alert if the ambient light readings that are taken exceed a threshold. The threshold is predefined and/or user configurable. The alert informs the person, or his or her caregiver, that sensor unit 20 and/or 120 may not be properly attached. The alert may be locally emitted by sensor unit 20, such as via an audio or visual indication (or both), and/or sensor unit 20 and 120 may transmit an alert message to a remote device, such as device 60, which then issues the alert. When transmitted remotely, the alert may include a text message and/or email transmitted to one or more caregivers assigned to the person wearing sensor unit 20 or 120.

In addition to detecting pulse wave velocity data, sensor units 20 and/or 120 are adapted in several embodiments to detect additional data. In one embodiment, sensor units 20 and 120 additionally include one or more temperature sensors coupled to patch 32 and/or substrate 70. These temperature sensors measure the temperature of the patient at the location of sensor units 20 and 120. This temperature data is made available for display on sensor unit 20 and/or 120 (if equipped with a local display), or it is transmitted to a remote device, such as device 60, for recording, processing, and/or displaying.

In another embodiment, sensor units 20 and/or 120 are adapted to include one or more sensors that detect the person's respiration rate. Such respiration rate sensors—which may be any known type of sensor used for detecting respiration rate—are included on patch 32 and/or substrate 70 and used to determine the respiration rate of the person to whom sensor unit 20 and/or 120 is coupled. As with the temperature sensor outputs, the respiration rate data is made available for display on sensor unit 20 and/or 120 (if equipped with a local display), or it is transmitted to a remote device, such as device 60, for recording, processing, and/or displaying. Both respiration rate sensors and temperature sensors are included with sensor units 20 and/or 120 in at least one embodiment, while in other embodiments sensor units 20 and/or 120 include only the respiration rate sensors or only the temperature sensors (in addition to pulse wave sensors 30).

In addition to determining the pulse wave velocity of a person, controllers 26 and/or 126 are adapted to use the outputs from detectors 36 to determine other physiological parameters of the person, in at least one embodiment. For example, in at least one embodiment, controllers 26 and/or 126 utilize the pulse wave velocity readings to determine a person's blood pressure. Any known techniques for converting pulse wave velocity readings to blood pressure may be utilized.

Still further, in at least one embodiment, one or more of controllers 26, 126, and/or processor 64 is configured to determine the person's blood pressure from the pulse wave readings by combining the pulse wave readings with one or more blood pressure readings made from an external source. The external source may be a conventional sphygmomanometer having an inflatable cuff, or any other known type of blood pressure detecting device. The readings from this external source are forwarded to controller 26, 126, and/or processor 64 and used to correlate the pulse wave readings to the person's blood pressure. Once this correlation is established, controller 26, 126, and/or processor 64 are configured to subsequently generate independent blood pressure readings from the outputs of pulse wave sensors 30. In this manner, multiple blood pressure readings can be generated for a particular patient without requiring the use of the external source for all of those blood pressure readings.

Thus, as one example, a first blood pressure reading using a conventional sphygmomanometer can be taken and used to calibrate sensor units 20 and/or 120, and then multiple subsequent readings of the person's blood pressure can be taken using sensor unit 20 and/or 120 without having to re-measure the person's blood pressure using the conventional sphygmomanometer. This can be especially advantageous by avoiding the need for repetitively inflating and deflating the inflatable cuff of the conventional sphygmomanometer, which can be discomforting and/or distracting to the patient.

Figure 5:
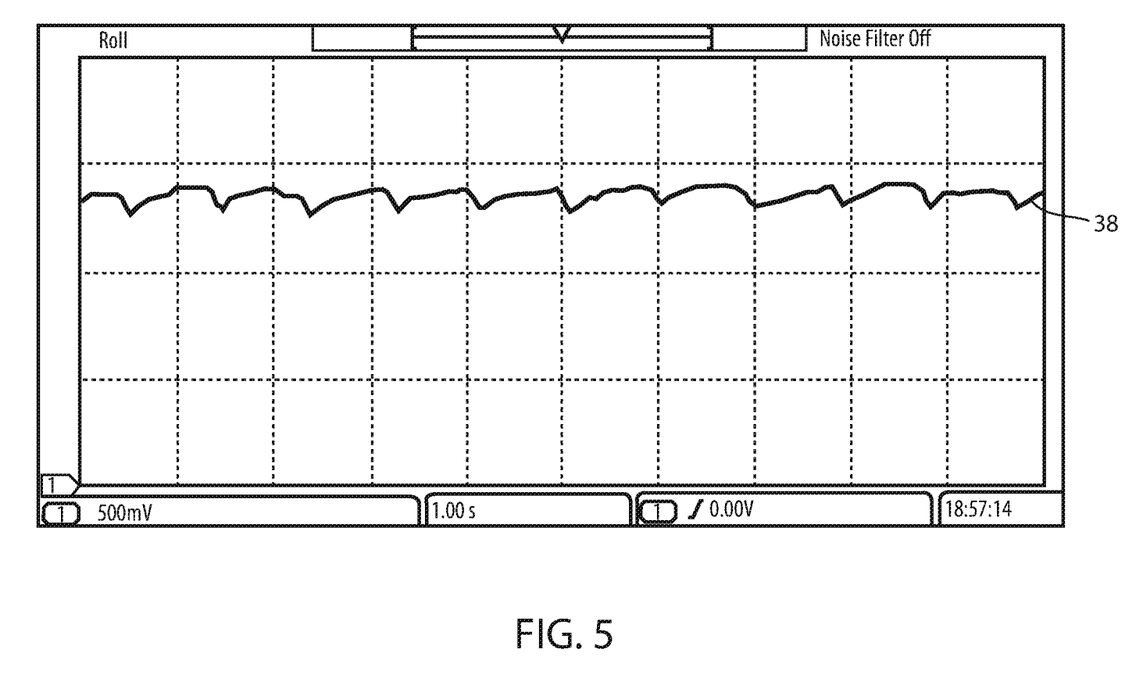
FIG. 5 is an illustrative diagram of an output from one of the emitter-detector pairs of the sensor unit of FIG. 1.

Controllers 26, 126, and/or processor 66 can also be configured in any of the embodiments disclosed herein to analyze the waveform 38 generated from either of pulse wave sensors 30 to determine the person's heart rate. As can be seen in FIG. 5, the person's heart rate is clearly visible from the troughs in waveform 38 and can be easily calculated using any suitable processing.

Controllers 26 and/or 126 are also configured in one embodiment to display and/or transmit to a remote device information indicative of the depth at which the pulse wave readings are being measured by pulse wave sensors 30. That is, controllers 26 and/or 126 are configured to store and/or transmit information indicating which subset of detectors 36 were used for the pulse wave readings taken by sensors 30. This information can be useful when comparing different sets of readings taken at different times, whether those readings are of the same person or for different persons.

In still another embodiment, sensor units 20 and/or 120 are integrated into a top surface of a mattress, cushion, or other surface on which a person lies, sits, or is otherwise positioned. That is, patch 32 and/or substrate 70 are constructed to be part of, if not the same as, the fabric or other material which forms the top surface of the cushion or mattress. Sensor units 20 and/or 120 are integrated therein such that emitters 34 face upward toward the person and are likely to come into contact with the person's skin when he or she sit or lies down on the mattress or cushion. In this manner, it is not necessary to physically secure the sensor unit 20 and/or 120 to the person. Instead, pulse wave readings can be taken at any time so long as the person remains in contact with the portion of the mattress or cushion in which the sensor unit 20 and/or 120 is integrated. In some embodiments, multiple sensor units 20 and/or 120 are integrated into the cushion or mattress so that if the person shifts his or her position on the cushion or mattress such that one of the sensor units is not able to take a pulse wave reading, at least one other sensor unit will likely still be able to take pulse wave readings. The inclusion of multiple sensor units 20 and/or 120 therefore facilitates continuous, or near continuous, pulse wave readings without requiring the person to remain stationary.

One or more sensor units 20 and/or 120 may also be used to determine vascular conditions that may be localized to one or more specific regions of a person's body. For example, a sensor unit 20 and/or 120 may be applied to the right leg of a person in order to determine that person's pulse wave velocity in his or her right leg. Thereafter, the sensor unit 20 and/or 120 can be applied to the left leg in order to determine that person's pulse wave velocity in his or her left leg. The readings from the right and left legs can then be compared to determine the relative vascular health of each of the person's legs. Significant differences in the two readings provide an indication of a localized vascular condition in one of the legs, such as a clot, poor circulation, or other conditions. Similarly, pulse wave velocity readings from other parts of the person's body, such as his or her arms and/or torso, can be compared to the leg readings and/or to each other to determine if there are any clinically significant disparities in the readings, thereby providing an indication of a localized vascular condition. Such comparison of readings may be done manually by a clinician viewing the pulse wave readings from the different locations on the patient's body, or it may be done automatically via one or more algorithms programmed into any of controllers 26, 126, and/or processor 66.

In still other embodiments, sensor units 20, 120, and/or device 60 are configured with a user interface enabling a user to input information about the pulse wave readings taken by sensor unit 20 and/or 120. Such information may include the identity of the person whose pulse wave velocity readings are being measured and recorded. Such information may also include the location on the person's body where the pulse wave readings are being taken. Still further, such information may include the time and date when the pulse wave readings are, or were, being taken. In still other embodiments, sensor units 20 and/or 120 include a clock that controller 26 and/or 126 use to automatically time stamp all of the pulse wave readings that are taken.

In still another embodiment, sensor unit 20 and/or 120 is configured to also take saturation of peripheral oxygen ($SpO_2$) readings of the person. In order to determine the person's oxygen saturation, sensor unit 20 and/or 120 may be modified to emit two frequencies of light, one having a wavelength of approximately 660 nm and the other having a wavelength of approximately 940 nm. The light that is scattered from each of these emitters is detected and the ratio of the detected 660 nm light to the 940 nm light is determined. From this ratio, the person's $SpO_2$ can be determined in known manners.

In any of the various embodiments described herein, sensor unit 20, 120, and/or processor 66 can be configured to analyze the data from pulse wave sensors 30 to predict and/or detect one or more additional health conditions regarding the patient. As one example, controllers 26, 126, and/or processor 66 can be configured to determine the patient's arterial stiffness based upon the pulse wave velocity readings. One method in which the arterial stiffness can be determined is through the use of the Moens-Korteweg equation, which relates the pulse wave velocity to the arterial stiffness. Other methods can be used. Controllers 26, 126, and/or processor 66 are configured in some embodiments to monitor and display trends in the person's arterial stiffness over time. Trends in the stiffness that exceed one or more predetermined criteria are automatically detected by controllers 26, 126, and/or processor 66 and appropriate alerting is provided.

In other embodiments, controllers 26, 126, and/or processor 66 are configured to analyze the morphology of the waveform 38 generated by one or both of pulse wave sensors 30 and monitor changes in this morphology over time. Changes in the morphology can be indicative of a potential problem with the patient's heart valves, the possibility of a future heart attack and/or aneurysm, internal bleeding, and/or other health conditions.

Controllers 26, 126, and/or processor 66 are also configured in various embodiments to determine and record the person's heart rate variability, the presence of edema in the tissue adjacent the pulse wave sensors 30, and/or whether or not the person is in a state of shock.

Sensor units 20 and/or 120 may also be used as diagnostic tools that gather and record data regarding a person's pulse wave velocity, arterial stiffness, heart rate variability, blood pressure, and/or other vascular conditions substantially continuously during a one or more medical events experienced by the patient, such as during or after surgery, a heart attack, a stroke, a seizure, or some other medical event.

In still other embodiments, sensor unit 20 and/or 120 is incorporated into an article of clothing, such as a sweatband, athletic apparel, Spandex shirts or pants, or other items of clothing. The incorporation therein allows pulse wave sensors 30 to non-invasively and unobtrusively take repetitive measurements of the wearer's pulse wave velocity and/or other vascular-related parameters. The gathered data is easily transferred to a smart phone, wristband monitor, computer, or other device via transmitter 28 and/or wireless module 58.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A sensor unit adapted to be non-invasively coupled to a patient, the sensor unit comprising:
   a first light emitter;
   a plurality of first light detectors, the plurality of first light detectors adapted to detect a portion of first light that is emitted by the first light emitter and scattered by direct contact with the patient, the plurality of first light detectors including a first light detector spaced a first distance from the first light emitter and a second light detector spaced a second distance from the first light emitter, the second distance being different from the first distance;
   a second light emitter spaced from the first light emitter a known distance;
   a plurality of second light detectors, the plurality of second light detectors adapted to detect a portion of second light emitted by the second light emitter and scattered by direct contact with the patient, the plurality of second light detectors including a third light detector spaced the first distance from the second light emitter and a fourth light detector spaced the second distance from the second light emitter; and
   a controller in communication with the plurality of first light detectors and with the plurality of second light detectors, the controller adapted to automatically select the first and third light detectors or the second and the fourth light detectors and to use outputs from the selected light detectors, but not the non-selected light detectors, in combination with the known distance to determine a pulse wave velocity of the patient.

2. The sensor unit of claim 1 wherein the controller selects between the first and third light detectors or the second and fourth light detectors a based upon an orientation of the sensor unit relative to the patient's adjacent arterial structure.

3. The sensor unit of claim 1 further including a transmitter, the transmitter adapted to transmit the pulse wave velocity to at least one of the following: a cell phone, a computer, a patient support apparatus, and a local area network.

4. The sensor unit of claim 1 wherein the controller is adapted to repetitively determine the pulse wave velocity of the patient.

5. The sensor unit of claim 4 wherein the controller is further adapted to detect changes in the pulse wave velocity of the patient over time.

6. The sensor unit of claim 1 wherein the first light and second light have wavelengths between 600 and 1000 nanometers.

7. The sensor unit of claim 1 wherein the controller is further adapted to measure at least one of the following patient conditions: a saturation of peripheral oxygen ($SpO_2$) level; a temperature; a respiration rate; a heart rate; and a blood pressure.

8. The sensor unit of claim 1 wherein the first and second light emitters and the pluralities of first and second light detectors are all integrated into a surface of one of a mattress and a cushion.

9. The sensor unit of claim 1 wherein the first light emitter, the plurality of first light detectors, the second light emitter, and the plurality of second light detectors are all integrated into a common housing.

10. The sensor unit of claim 1 wherein the controller automatically selects the first and third light detectors if the first light detector outputs a signal having a greater strength than a signal output by the second light detector, and the controller automatically selects the second and fourth light detectors if the signal output by the second light detector has a greater strength than the signal output by the first light detector.

11. A sensor unit adapted to be non-invasively coupled to a patient, the sensor unit comprising:
- a first light emitter;
- a plurality of first light detectors, the plurality of first light detectors adapted to detect a portion of first light that is emitted by the first light emitter and scattered by direct contact with the patient, the plurality of first light detectors including a first light detector spaced a first distance from the first light emitter and a second light detector spaced a second distance from the first light emitter, the second distance being different from the first distance;
- a second light emitter spaced from the first light emitter a known distance;
- a plurality of second light detectors, the plurality of second light detectors adapted to detect a portion of second light emitted by the second light emitter and scattered by direct contact with the patient, the plurality of second light detectors including a third light detector spaced the first distance from the second light emitter and a fourth light detector spaced the second distance from the second light emitter; and
- a controller in communication with the plurality of first light detectors and with the plurality of second light detectors, the controller adapted to allow a user to select the first and third light detectors or the second and the fourth light detectors and to use outputs from the selected light detectors, but not the non-selected light detectors, in combination with the known distance to determine a pulse wave velocity of the patient.

12. The sensor unit of claim 11 further comprising:
- a housing;
- a transmitter contained within the housing, the transmitter adapted to transmit data generated from the first and second plurality of light detectors to a remote device; and
- a patch physically coupled to the housing, the patch comprising a flexible membrane and an adhesive coating coupled to a side of the flexible membrane, the patch adapted to secure the first light emitter, the first plurality of light detectors, the second light emitter, and the second plurality of light detectors to the skin of the patient.

13. The sensor unit of claim 12 wherein the transmitter is a wireless transmitter.

14. The sensor unit of claim 12 wherein the transmitter is built from flexible electronics adapted to bend and follow the flexibility of the patch.

15. The sensor unit of claim 12 wherein the patch further includes a temperature sensor adapted to measure a temperature of the patient at the location of the patch, wherein the transmitter is further adapted to transmit readings from the temperature sensor to the remote device.

16. The sensor unit of claim 12 wherein the patch further includes a respiration rate sensor adapted to measure a respiration rate of the patient, wherein the transmitter is further adapted to transmit readings from the respiration rate sensor to the remote device.

\* \* \* \* \*

UNITED STATES PATENT AND TRADEMARK OFFICE
CERTIFICATE OF CORRECTION

| | | |
|---|---|---|
| PATENT NO. | : 10,820,859 B2 | Page 1 of 1 |
| APPLICATION NO. | : 14/884222 | |
| DATED | : November 3, 2020 | |
| INVENTOR(S) | : Sean Hadley et al. | |

It is certified that error appears in the above-identified patent and that said Letters Patent is hereby corrected as shown below:

In the Claims

Column 16
Claim 2, Line 38, delete "a" before --based upon an orientation--

Signed and Sealed this
Fifteenth Day of October, 2024

Katherine Kelly Vidal
*Director of the United States Patent and Trademark Office*